United States Patent
Tanaka et al.

(10) Patent No.: US 7,084,295 B2
(45) Date of Patent: Aug. 1, 2006

(54) PERFLUOROADAMANTYL ACRYLATE COMPOUND AND INTERMEDIATE THEREFOR

(75) Inventors: Shinji Tanaka, Chiba (JP); Toshihide Yoshitome, Chiba (JP); Kouichi Kodoi, Chiba (JP); Hidetoshi Ono, Chiba (JP); Naoyoshi Hatakeyama, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 39 days.

(21) Appl. No.: 10/499,305

(22) PCT Filed: Dec. 20, 2002

(86) PCT No.: PCT/JP02/13378

§ 371 (c)(1),
(2), (4) Date: Jan. 26, 2005

(87) PCT Pub. No.: WO03/055541

PCT Pub. Date: Jul. 10, 2003

(65) Prior Publication Data

US 2005/0131247 A1  Jun. 16, 2005

(30) Foreign Application Priority Data

Dec. 25, 2001 (JP) .............................. 2001-390972
Jul. 30, 2002 (JP) .............................. 2002-220729
Jul. 30, 2002 (JP) .............................. 2002-324257

(51) Int. Cl.
*C07C 69/00* (2006.01)
(52) U.S. Cl. .................................................. 560/219
(58) Field of Classification Search ................. 560/219
See application file for complete search history.

(56) References Cited

U.S. PATENT DOCUMENTS 3,600,433 A   8/1971   Holland et al.

FOREIGN PATENT DOCUMENTS

JP     63-307844     12/1988

OTHER PUBLICATIONS

James L Adcock and Huqiu Zhang Highly Fluorinated Adamantanols: Synthesis, Acidities, and Reactivities J.Org. Chem. 1996,61,5073-5076.*
James L. Adcock and Huimin Luo Synthesis and Nucleophilic and Photochemical Reactions of F-Adamantanone J.Org.Chem. 1992, 57,4297-4300.*
Adcock, James L. et al., Highly Fluorinated Adamantanols: Synthesis, Acidities, and Reactivities, Journal of Organic Chemistry, 1996, vol. 61, No. 15, pp. 5073 to 5076.
Adcock, James L. et al., Synthesis and nucleophilic and photochemical reactions of F-adamantanone, Journal of Organic Chemistry, 1992, vol. 57, No. 15, pp. 4297 to 4300.

* cited by examiner

*Primary Examiner*—Samuel A Barts
*Assistant Examiner*—Lalitha Nagubandi
(74) *Attorney, Agent, or Firm*—Oblon, Spivak, McClelland, Maier & Neustadt, P.C.

(57) ABSTRACT

A perfluoroadamantyl acrylate compound which is highly useful as a raw material for functional resins,etc.;and an intermediate therefore. The perfluoroadamantyl acrylate compound comprises perfluoroadamantane having a $CH_2=C(R)COO$ group(wherein R is a hydrogen atom, a methyl group or a trifluoromethyl group) at the 1-position, at each of the 1- and 3-positions, at each of the 1-, 3- and 5-positions, at each of the 1-, 3-, 5- and 7-positions, or at the 2-position.

3 Claims, No Drawings

PERFLUOROADAMANTYL ACRYLATE COMPOUND AND INTERMEDIATE THEREFOR

TECHNICAL FIELD

The present invention relates to a novel perfluoroadamantyl compound and an intermediate therefor, and more particularly, to a novel perfluoroadamantyl compound and an intermediate therefor that are highly useful as a raw material for functional resins.

BACKGROUND ART

It is known that an acrylic ester and a methacrylic ester each having an adamantane skeleton can be polymerized into a polymer which is excellent in heat resistance, mechanical strength such as impact resistance and surface hardness and optical characteristics. For instance, Japanese Patent Laid-Open Application {No. 307844/1988 (Showa 63)} proposes a diacrylate and dimethacrylate having a halogen atom or a hydroky group at each of the 5-position of the adamantane skeleton or at each of the 7-position of the same. The acrylic ester and methacrylic ester each having the above-mentioned structural unit, which are colorless and transparent and have high a surface hardness and also large refractive index, are highly useful as a raw material for optical instruments and members such as lens, prisms, photosensitive materials, optical fiber and optical discs. In addition, the acrylic ester and methacrylic ester as mentioned above have each a surpassingly high melting point and surface hardness as compared with the acrylic ester and methacrylic ester that are being generally used, are highly useful as a material of a heat resistant covering and forming for an acrylic ester and methacrylic ester. However the aforesaid useful acrylic ester and methacrylic ester suffer from a disadvantage of insufficient transparency in a low wavelength region.

As mentioned hereinbefore, the acrylic ester and a methacrylic ester each having an adamantane skeleton which is imparted with a specific chemical structure are highly useful as a raw material for a functional resin. However it is desired to develop an acrylic ester and a methacrylic ester which have any of various chemical structures and which are capable of being made into an acrylic ester and a methacrylic ester, respectively that are enhanced in such functionality as optical properties and heat resistance.

DISCLOSURE OF THE INVENTION

An object of the present invention is to provide a perfluoroadamantyl acrylate compound which is highly useful as a material for functional resins and the like; and an intermediate therefor.

As the result of intensive extensive research and investigation accumulated by the present inventors in order to achieve the object as mentioned above, it has been found that a perfluoroadamantyl acrylate compound having a specific chemical structure can achieve the above-mentioned object. Thus the present invention has been accomplished on the basis of the foregoing findings and information.

Specifically, the gist of the present invention is as follows.

(1) A perfluoroadamantyl acrylate compound represented by the following general formula (1)

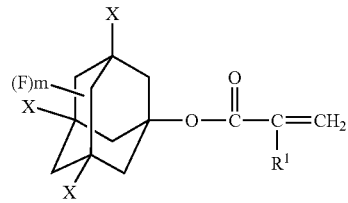

wherein $R^1$ is a hydrogen atom, a methyl group or a trifluoromethyl group; X is a fluorine atom, a hydroxy group or a $CH_2=C(R)COO$ group, wherein R is a hydrogen atom, a methyl group or a trifluoromethyl group; and m is an integer of from 12 to 15.

(2) A perfluoroadamantyl acrylate compound represented by the following general formula (2)

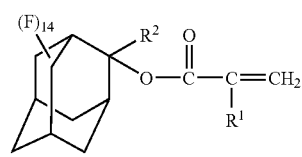

wherein $R^1$ is a hydrogen atom, a methyl group or a trifluoromethyl group; and R 2 is a hydrogen atom, a methyl group, an ethyl group or a perfluoroalkyl group having 1 to 4 carbon atoms.

(3) A perfluoroadamantanol compound represented by the following general formula (3)

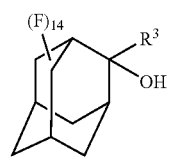

wherein $R^3$ is a methyl group, an ethyl group or a perfluoroalkyl group having 1 to 4 carbon atoms.

THE MOST PREFERRED EMBODIMENT TO CARRY OUT THE INVENTION

The perfluoroadamantyl acrylate compound according to the present invention is that represented by the above-mentioned general formula (1) or (2). Moreover the perfluoroadamananol compound according to the present invention is an intermediate (starting raw material) of the perfluoroadamantyl acrylate compound represented by the above-mentioned general formula (2), and is represented by the above-mentioned general formula (3). Herein, examples of the perfluoroalkyl group which is represented by $R^2$ or $R^3$ and has 1 to 4 carbon atoms include a trifluoromethyl group, a pentafluoroethyl group, a heptafluoropropyl group and a nonafluorobutyl group.

The perfluoroadamantyl acrylate -compounds represented by the general formula (1) according to the present invention are specifically exemplified by

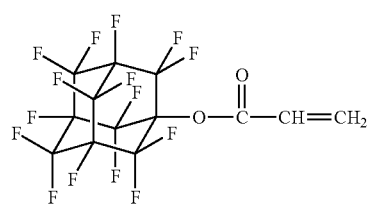
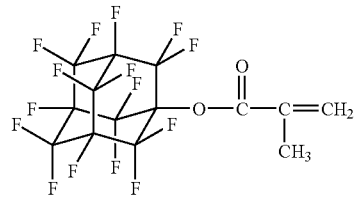
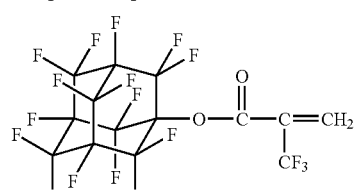
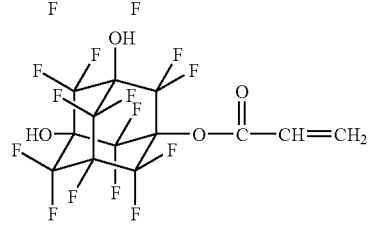
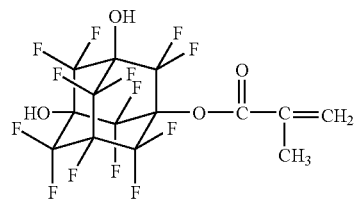
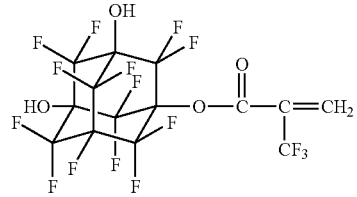
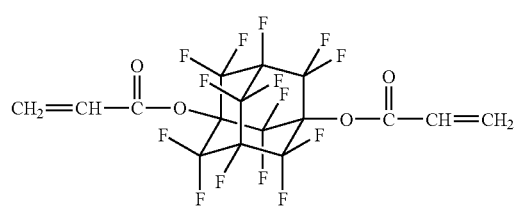
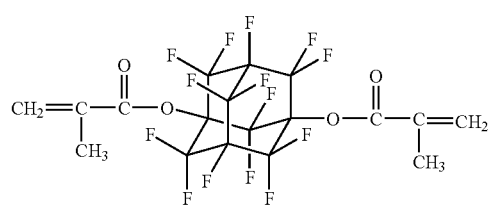
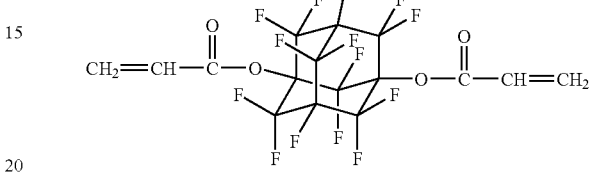
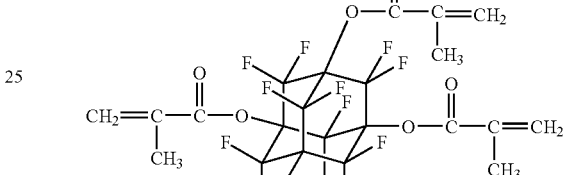
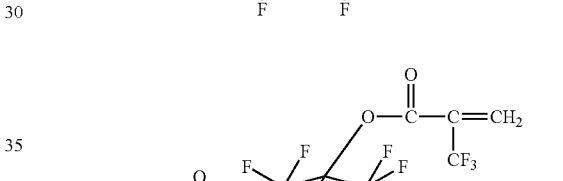
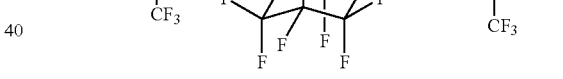
The perfluoroadamantyl acrylate compounds represented by the general formula (2) according to the present invention are specifically exemplified by
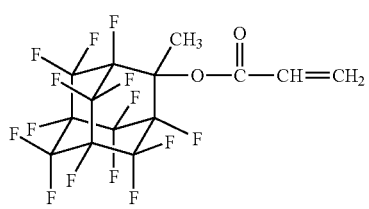
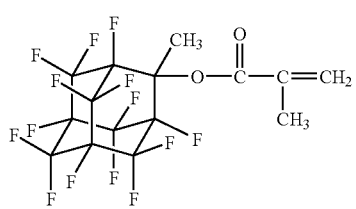

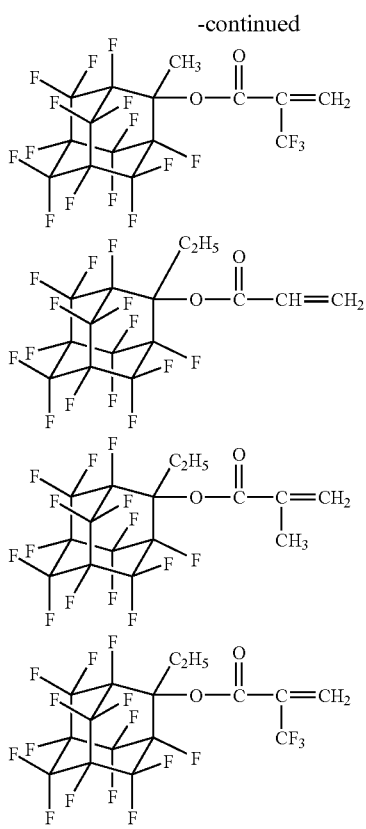

The perfluoroadamantyl acrylate compounds represented by the general formula (3) according to the present invention are specifically exemplified by 2-methyl-2-perfluoroadamantanol, 2-ethyl-2-perfluoroadamantanol, 2-trifluoromethyl-2-perfluoroadamantanol, 2-pentafluoroethyl-2-perfluoroadamantanol, 2-heptafluoropropyl-2-perfluoroadamantanol, and 2-nonafluorobutyl-2-perfluoroadamantanol.

Next, a process for producing a perfluoroadamantyl acrylate compound represented by the general formula (1) can be in accordance with a process which comprises azeotropically dehydrating a perfluoroadamantanol and an acrylic acid or an analog thereof under reflux of a solvent. Examples of the perfluoroadamantanol to be used as a starting raw material include perfluoro-1-adamantanol, perfluoro-1,3-adamantandiol, perfluoro-1,3,5-adamantantriol and perfluoro-1,3,5,7-adamantantetraol. Examples of the acrylic acid or an analog thereof include acrylic acid, methacrylic acid and α-trifluoromethyl acrylate. As a reaction solvent, toluene and xylene are preferably used.

In addition, the reaction conditions in this case, which are similar to those in a general azeotropical dehydration reaction, can be set on a reaction temperature in the range of minus 78 to 200° C., but is preferably set on the boiling point of the solvent at the reaction pressure at this time, including a reaction pressure in the range of 0.1 to 10 MPa, a reaction time in the range of 1 to 24 hours, preferably 3 to 6 hours. The concentration of the starting raw material to be dissolved in the reaction solvent needs only to be within the saturated solubility without specific limitation, but is preferably in the range of 0.5 to 1.0 mol/liter.

In a process for producing the perfluoroadamantyl acrylate compound represented by the general formula (2) according to the present invention, the starting raw material needs only to use a perfluoroadamantanol such as
  2-H-2-perfluoroadamantanol, 2-methyl-2-perfluoroadamantanol,
  2-ethyl-2-perfluoroadamantanol, 2-trifluoromethyl-2-perfluoroadamantanol and
  2-pentafluoroethyl-2-perfluoroadamantanol, and the reaction conditions in this case need only to be similar to the foregoing.

Further, the reaction of the perfluoroadamantanol and the acrylic acid or analogues in the production of these perfluoroadamantyl acrylate compounds may be put into practice by dehydration esterification by the use of a dehydrating agent. In the case of this production process, the dehydrating agent is preferably selected for use from molecular sieves that are used for general dehydration esterification and acidic dehydrating agents such as sodium sulfate anhydride, magnesium sulfate anhydride and phosphoric acid anhydride. As a reaction solvent, use is made of an ether base solvent such as diethyl ether, tetrahydrofuran and dioxane; and an aliphatic hydrocarbon base solvent such as hexane, heptane and octane; and aromatic hydrocarbon base solvent such as benzene, toluene and xylene. In addition, the reaction conditions in this case can be set on a reaction temperature in the range of minus 78 to 200° C., but is preferably set in the range of room temperature to the boiling point of the solvent at the reaction pressure at this time, including a reaction pressure in the range of 0.1 to 10 MPa, preferably atmospheric pressure, a reaction time in the range of 1 to 24 hours, preferably 3 to 6 hours. The concentration of the starting raw material to be dissolved in the reaction solvent needs only to be within the saturated solubility without specific limitation, but is preferably in the range of 0.5 to 1.0 mol/liter.

The perfluoroadamantyl acrylate compounds can be produced by esterification reaction in the presence of a base between a perfluoroadamantanol and an acrylic acid chloride or an analog thereof. Examples of the base to be used therein include trimethylamine, triethylamine, pyridine and N,N-dimethylaniline. As a reaction solvent, which is not always necessary, use can be made of halogenated hydrocarbons such as dichloromethane, carbon terachloride and 1,2-dichloroethane; an ether base solvent such as diethyl ether, tetrahydrofuran and dioxane; and an aliphatic hydrocarbon base solvent such as hexane, heptane and octane; and aromatic hydrocarbon base solvent such as benzene, toluene and xylene. In addition, the reaction conditions in this case can be set on a reaction temperature in the range of minus 78 to 100° C., but is preferably set in the range of minus 78 to room temperature, including a reaction pressure in the range of 0.1 to 10 MPa, a reaction time in the range of 1 to 24 hours, preferably 1 to 3 hours. In the case where a reaction solvent is used, the concentration of the starting raw material to be dissolved in the reaction solvent needs only to be within the saturated solubility without specific limitation, but is preferably in the range of 0.5 to 1.0 mol/liter.

The perfluoroadamantyl acrylate compounds can be produced by esterification reaction between a perfluoroadamantyl alkoxide and an acrylic acid chloride or an analog thereof. As a reaction solvent, use can be made of an aliphatic hydrocarbon base solvent such as hexane, heptane and octane; and aromatic hydrocarbon base solvent such as benzene, toluene and xylene. In addition, the reaction conditions in this case can be set on a reaction temperature in the range of minus 78 to 100° C., but is preferably set in the range of minus 78 to room temperature, including a reaction pressure in the range of 0.1 to 10 MPa, a reaction time in the range of 1 to 24 hours, preferably 1 to 3 hours. In the case where a reaction solvent is used, the concentration of the starting raw material to be dissolved in the reaction solvent needs only to be within the saturated solubility without specific limitation, but is preferably in the range of 0.5 to 1.0 mol/liter.

The perfluoroadamantyl alkoxide to be used in the reaction can be produced by reacting the above-mentioned perfluoroadamantanol with an alkoxiding agent. As the alkoxiding agent, use is made of metallic lithium, metallic sodium, metallic potassium, n-butyllithium, sec-butyllithium, tert-butyllithium, sodium hydroxide, sodium hydride, sodium boron hydride and lithium-alumnum hydride. As a reaction solvent, use is made of an ether base solvent such as diethyl ether, tetrahydrofuran and dioxane; an aliphatic hydrocarbon base solvent such as hexane, heptane and octane; and aromatic hydrocarbon base solvent such as benzene, toluene and xylene.

The acrylic acid chloride or an analog thereof to be used in the reaction can be produced by reacting a chlorinating agent with the above-mentioned acrylic acid chloride or an analog thereof. As the chlorinating agent, there are preferably used thionyl chloride, phosphorus pentachloride, phosphorus trichloride, benzoic acid chloride and phthalic acid chloride. In this reaction, as a reaction solvent, which is not always necessary, use can be made of halogenated hydrocarbons such as dichloromethane, chloroform, carbon terachloride and 1,2-dichloroethane; an aliphatic hydrocarbon base solvent such as hexane, heptane and octane; and aromatic hydrocarbon base solvent such as benzene, toluene and xylene. There may be used as necessary, a catalyst such as N,N-dimethylformamide, hexamethylphosphoric triamide and pyridine; and a reaction accelerator such as benzyltriethylammonium chloride.

In addition, the reaction conditions in this case can be set on a reaction temperature in the range of 0 to 200° C., preferably room temperature to 100° C., including a reaction pressure in the range of 0.1 to 10 MPa, a reaction time in the range of 1 to 24 hours, preferably 1 to 6 hours. In the case where a reaction solvent is used, the concentration of the starting raw material to be dissolved in the reaction solvent needs only to be within the saturated solubility without specific limitation, but is preferably in the range of 0.5 to 1.0 mol/liter.

In the last place, description will be given of some processes for producing the perfluoroadamantanol represented by the general formula (3), wherein perfluoro-2-adamantanone is used in every case as a starting raw material.

(1) In the Case of $R^3$ Being a Methyl Group or an Ethyl Group (a) Addition Reaction to Carbonyl Group with a Grignard Reagent The starting raw material and the Grignard reagent are reacted in a solvent and the reaction product is hydrolyzed with an acid. As a reaction solvent, use is made of an ether base solvent such as diethyl ether, tetrahydrofuran and dioxane; an aliphatic hydrocarbon base solvent such as hexane, heptane and octane; and aromatic hydrocarbon base solvent such as benzene, toluene and xylene. As a Grignard reagent, use is made of an alkyl magnesium chloride (RMgCl), alkyl magnesium bromide (RMgBr) and alkyl magnesium iodide (RMgI). The reaction conditions in the first half stage include atmospheric pressure, reaction temperature in the range of minus 78 to 200° C., preferably 0° C. to room temperature, a reaction time in the range of 1 to 24 hours. In the case where a reaction solvent is used, the concentration of the starting raw material to be dissolved in the reaction solvent needs only to be within the saturated solubility without specific limitation, but is preferably in the range of 0.5 to 1.0 mol/liter.

(b) Addition Reaction to Carbonyl Group with a Lithium Reagent

The starting raw material and the lithium reagent are reacted in a solvent and the reaction product is hydrolyzed with an acid. As a reaction solvent, use is made of an ether base solvent such as diethyl ether, tetrahydrofuran and dioxane; an aliphatic hydrocarbon base solvent such as hexane, heptane and octane; and aromatic hydrocarbon base solvent such as benzene, toluene and xylene. As a lithium reagent, use is made of an alkyl lithium (RLi) and dialkylmethylmagnesium cuprate ($R_2LiCu$). The reaction conditions in the first half stage include atmospheric pressure, reaction temperature in the range of minus 78 to 200° C., preferably 0° C. to room temperature, a reaction time in the range of 1 to 24 hours. In the case where a reaction solvent is used, the concentration of the starting raw material to be dissolved in the reaction solvent needs only to be within the saturated solubility without specific limitation, but is preferably in the range of 0.5 to 1.0 mol/liter.

(2) In the Case of $R^3$ Being Rf (perfluoroalkyl group: $CF_3$~$C_4F_9$)

(a) Addition Reaction to Carbonyl Group with a trimethylsilanyl perfluoroalkane [$RfSi(CH_3)_3$]

The starting raw material and the trimethylsilanyl perfluoroalkane [$RfSi(CH_3)_3$] are reacted in a solvent in the presence of a catalyst, and the reaction product is hydrolyzed with an acid. As a reaction solvent, use is made of an ether base solvent such as diethyl ether, tetrahydrofuran and dioxane; an aliphatic hydrocarbon base solvent such as hexane, heptane and octane; and aromatic hydrocarbon base solvent such as benzene, toluene and xylene. As a catalyst, use is made of tetrabutylammonium fluoride [$(C_4H_9)_4NF$]. The reaction conditions in the first half stage include atmospheric pressure, reaction temperature in the range of usually minus 78 to 200° C., preferably 0° C. to room temperature, a reaction time in the range of usually 1 to 24 hours. In the case where a reaction solvent is used, the concentration of the starting raw material to be dissolved in the reaction solvent needs only to be within the saturated solubility without specific limitation, but is preferably in the range of 0.5 to 1.0 mol/liter.

(b) Addition Reaction to Carbonyl Group with a perfluoroalkyl iodide (RfI)

The starting raw material and the perfluoroalkyl iodide (RfI) are reacted in a solvent in the presence of a catalyst, and the reaction product is hydrolyzed with an acid. As a reaction solvent, use is made of an ether base solvent such as diethyl ether, tetrahydrofuran and dioxane; an aliphatic hydrocarbon base solvent such as hexane, heptane and octane; N,N-dimethylformamide and dimethylsulfoxide. As a catalyst, use is made of Zinc (Zn)/dicyclopentadienyltitanium dicloride ($Cp_2TiCl_2$) (coexisting system). The reaction conditions in the first half stage include atmospheric pressure, reaction temperature in the range of usually minus 78 to 200° C., preferably 0° C. to 100° C., a reaction time in the range of usually 1 to 24 hours. In the case where a reaction solvent is used, the concentration of the starting raw material to be dissolved in the reaction solvent needs only to be within the saturated solubility without specific limitation, but is preferably in the range of 0.5 to 1.0 mol/liter. It is preferable in this reaction to simultaneously apply ultrasonic activation by means of a ultrasonic cleaner.

The perfluoroadamantyl acrylate compound obtainable in the above-mentioned manner according to the present invention is excellent in such characteristics as heat stability, chemical stability, lubricity and electrical insulation properties and thus is highly useful in wide fields of raw materials for functional resins required of optical properties and heat resistance; resin additives such as heat resistance improvers; additives such as acidity enhancers and fat-solubility enhancers; coating materials such as paint and printing ink; lubricating oil; working oil; heating/heat transfer media; adhesives; covering materials for optical fiber; pharmaceuticals; agrochemicals; intermediates and so forth.

EXAMPLE

In what follows, the present invention will be described in more detail with reference to comparative examples and working examples, which however shall never limit the present invention thereto.

Example 1

In a 50 milliliter (mL) flask was placed 2.1 g (5.0 millimol) of perfluoroadamantanediol and then were added 10 mL of tetrahydrofuran as a solvent and 0.84 mL (6.0 millimol) of triethylamine as a base with stirring. Subsequently the flask was put in an ice bath, and 0.4 mL (5.0 millimol) of acrylic acid chloride was gradually added dropwise in the flask. When the acrylic acid chloride was added dropwise, a salt was immediately formed, causing the reaction liquid to become whitely turbid. After the lapse of 15 minutes from the end of the dropwise addition, the flask was taken out from the ice bath, and the mixture therein was reacted for 3 hours at room temperature with stirring. After the completion of the reaction, the resultant reaction liquid was filtered with a cannula equipped with a filter, and the inside of the flask was washed twice with 5 mL of tetrahydrofuran. Subsequently the solvent was evaporated away from the reaction liquid. Thus the reaction liquid was purified with a glass tube oven to obtain the objective perfluoro-1-adamantyl acrylate with a yield amount of 1.4 g (2.9 millimol) and a yield rate 59.0%.

As a result of analysis for the resultant perfluoro-1-adamantyl acrylate by nuclear magnetic resonance spectra (NMR), there were observed the following absorption.

$^1$H-NMR {270 MHz}: at 6.16 (dd, $J_{vic-trans}$=10.4 Hz, $J_{gem}$=1.5 Hz, 1H), 6.25 (dd, $J_{vic-trans}$=10.4 Hz, $J_{vis-cis}$=16.3 Hz, 1H), 6.64 (dd, $J_{vic-cis}$=16.3 Hz, $J_{gem}$=1.5 Hz, 1H). $^{13}$C-NMR {68 MHz}: at 123.4, 136.12, 157.47. $^{19}$F-NMR {254 MHz}: at −221.55 (s, 3F), −121.17 (s, 6F), −114.62 (s, 6F).

In addition, the results of gas-chromatography mass spectrometric analysis were 476 (M$^+$, 2.4%), 456 (1.8%), 55 (100%).

Example 2

The procedure in Example 1 was repeated to obtain the objective perfluoro-1-adamantyl acrylate except that 0.49 mL (5.0 millimol) of methacrylic acid chloride was used in place of the acrylic acid chloride as the starting raw material. The yield amount was 1.6 g (3.3 millimol) and yield rate 65.0%.

As a result of analysis for the resultant perfluoro-1-adamantyl acrylate by nuclear magnetic resonance spectra (NMR), there were observed the following absorption.

$^1$H-NMR {270 MHz}: at 3.03 (s, 3H), 5.88 (s 1H), 6.33 (s, 1H). $^{13}$C-NMR {68 MHz}: at 18.34, 130.46, 158.79. $^{19}$F-NMR {254 MHz}: at −221.65 (s, 3F), −121.18 (s, 6F), −114.55 (s, 6F).

In addition, the results of gas-chromatography mass spectrometric analysis were 490 (M$^+$, 20%), 471 (19%), 69 (100%).

Example 3

(1) Production of α-(trifluoromethyl)acrylic acid chloride

In a 200 mL flask was placed 42.0 g (300 millimol) of α-(trifluoromethyl) acrylic acid, to which was gradually added 70.0 mL (450 millimol) of phthalic dichloride at room temperature with stirring. Subsequently, by reacting the contents in the flask for 2 hours, while heating in an oil bath at 135° C., an orange reaction liquid was obtained.

Subsequently, by atmospherically distillating the reaction liquid, 41.2 g (yield rate 86.6%) of colorless transparent product in liquid form was obtained.

As a result of analysis for the resultant perfluoro-1-adamantyl acrylate by nuclear magnetic resonance spectra (NMR), there were observed the following absorption.

$^1$H-NMR {270 MHz}: at 6.91 (s, 1H), 7.11 (s, 1H). $^{13}$C-NMR {68 MHz}: at 120.91 (quar, $J_{C-F}$=273.9 Hz), 135.25 (quar, $J_{C-CF3}$=31.8 Hz), 139.28, 161.92.

Thereby, the colorless transparent product was identified as α-(trifluoromethyl)acrylic acid chloride.

(2) Production of perfluoro-1-adamantyl-α-(trifluoromethyl) acrylate

The procedure in Example 1 was repeated to obtain the objective perfluoro-1-adamantyl-α-(trifluoromethyl) acrylate except that 801 mg (5.1 millimol) of the α-(trifluoromethyl) acrylic acid chloride which had been obtained in the preceding item (1).

The yield amount was 1.2 g (2.2 millimol) and yield rate was 44%.

As a result of analysis for the resultant perfluoro-1-adamantyl-α-(trifluoromethyl) acrylate by nuclear magnetic resonance spectra (NMR), there were observed the following absorption.

$^1$H-NMR {270 MHz}: at 7.92 (quar, J=2.8 Hz, 1H), 8.04 (quar, J=2.8 Hz, 1H) $^{13}$C-NMR {68 MHz}: at 121.15 (quar, $J_{C-F}$=268.5 Hz), 131.85 (quar, $J_{C-CCF3}$=5.0 Hz), 132.74 (quar, $J_{C-CF3}$=31.8 Hz), 159.79. $^{19}$F-NMR {254 MHz}: at −221.51 (s, 3F), −121.99 (s, 6F), −114.44 (s, 6F), −66.41 (s, 3F)

In addition, the results of gas-chromatography mass spectrometric analysis were 544 (M$^+$, 5.4%), 523 (4.3%), 123 (100%).

Example 4

(1) Production of 2-methyl-2-perfluoroadamantanol

In a 500 mL Kjeldahl flask was placed 24.1 g (60 millimol) of 2-perfluoroadamantanone, to which was added 180 mL of dry diethyl ether to dissolve the same. Thereafter the flask was put in an ice bath and 21 mL (63 millimol) of 3 mol/liter solution of methylmagnesium bromide was added dropwise in the flask with stirring. After the lapse of 30 minutes, gas-chromatographic analysis was carried out with a result that the disappearance of the raw material peak was confirmed. After the reaction liquid was poured on ice water, dilute hydrochloric acid was added so as to dissolve inorganic substances in a water phase. Organic phase was separated with a separatory funnel and dried. Then by evaporating away the solvent, 22.9 g of a crude product was obtained, purified with a column, and recrystallized from methanol-hexane to obtain the objective product.

The yield amount was 8.1 g (19.4 millimol) and yield rate was 32.3%. Purity measured by gas chromatography was 84.1% [area].

As a result of analysis for the resultant 2-methyl-2-perfluoroadamantanol by nuclear magnetic resonance spectra (NMR), there were observed the following absorption.

$^1$H-NMR {500 MHz}: at 1.81 (s, 3H, CH$_3$), $^{13}$C-NMR {126 MHz}: at 19.68 (t, J=13.2 Hz, CH$_3$) $^{19}$F-NMR {471 MHz}: at −223.11 (s, 1F, d or e), −222.71(s, 1F d or e), −217.94 (s, 2F, a), −123.62 (quar,J=240 Hz, 1F), −121.11 (s, 2F, f), −118.52 (d,j=240 Hz, 1F), −117.46 (s, 1F), −116.90 (s, 1F), −116.34 (s, 1F), −114.39 (d,j=271 Hz, 2F)

In addition, the results of gas-chromatography mass spectrometric analysis were 418 (M$^+$, 0.38%), 403 (6.0%), 131 (85.2%), 69 (100%).

The melting point measured by DSC (differential scanning calorimetry) was 69.7 to 79.5° C.

As the result of structural analysis by the above-mentioned spectoscopic data, the following structural formula has been confirmed.

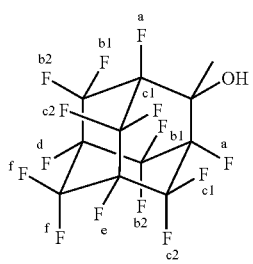

(2) Production of 2-methyl-2-perfluoroadamantyl methacrylate

In a 50 mL Kjeldahl flask was placed 0.836 g (2.0 millimol) of 2-methyl-2-perfluoroadamantanol, to which was added 20 mL of tetrahydrofuran to dissolve the same. Thereafter the flask was put in an ice bath, and 0.33 mL (2.4 millimol) of triethylamine and 0.22 mL (2.0 millimol) of methacrylic acid chloride were added in the flask to start stirring. After the lapse of 15 minutes, the ice bath was taken out, and the contents therein were reacted for further 48 hours at room temperature. The reaction liquid was filtered with fluted filter paper, and the flask was washed twice with 5 mL of diethyl ether. Salts were removed from the reaction liquid with a separatory funnel to recover organic phase. Then by distilling away the solvent and purifying with a column, the objective 2-methyl-2-perfluoroadamantyl methacrylate was obtained, The yield amount was 0.17 g (0.35 millimol) and yield rate was 17.5%. Purity measured by gas chromatography was 97.6% [area].

As a result of analysis for the resultant 2-methyl-2-perfluoroadamantyl methacrylate by nuclear magnetic resonance spectra (NMR, CDCl$_3$), there were observed the following absorption.

$^1$H-NMR {500 MHz}: at 1.93 (s, 3H, f), 2.16 (s, 3H, c), 5.71 (s, 1H, a1), 6.12 (s, 1H, a2) $^{13}$C-NMR {126 MHz}: at 15.04 (f), 18.31(c), 128.54 (a), 130.50(b), 162.32(d). $^{19}$F-NMR {471 MHz}: at −221.65 (s, 3F),−121.18 (s, 6F), −225.55 (s, 2F, g or j) −209.76 (s, 2F, j or g), −121.07 (s, 2F, k), −116.72(q, 6F,i), −114.03 (d, 2F, h)

In addition, the results of gas-chromatography mass spectrometric analysis were 486 (M$^+$, 1.4%), 400 (1.4%), 381 (2.4%), 181 (7.1%), 86 (100%).

The melting point measured by DSC (differential scanning calorimetry) was 54.7 to 57.1° C.

As the result of structural analysis by the above-mentioned spectoscopic data, the following structural formula has been confirmed.

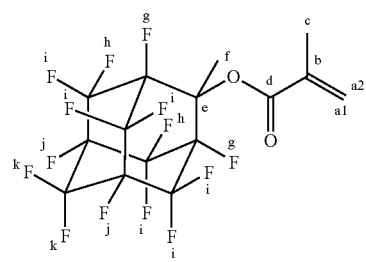

Example 5

In a 500 mL Kjeldahl flask was placed 62.3 g (150 millimol) of 1,3-perfluoroadamantandiol[1], to which was added 200 mL of diethy ether to dissolve the same. Thereafter the flask was put in an ice bath, and 25.1 mL (180 millimol) of triethylamine and 12.2 mL (150 millimol) of methacrylic acid chloride were added in the flask to start stirring. After the lapse of 1 hour, the ice bath was taken out, and the contents therein were reacted for further 15 hours at room temperature. The reaction liquid was filtered with fluted filter paper, and the flask was washed twice with 50 mL of diethyl ether. Salts were removed from the reaction liquid with a separatory funnel to recover organic phase. Then by evaporating away the solvent and purifying with a column, the objective 3-hydroxy-1-perfluoroadamantyl acrylate[2]) [actual yield amount of 18.6 g (39.2 millimol), yield rate of 26.1% and purity measured by gas chromatography being 96.5% {area}] and 1,3-perfluoroadamantyl diacrylate [actual yield amount of 8.6 g (16.2 millimol), yield rate of 10.8% and purity measured by gas chromatography being 95.3% {area}] were obtained, 1): contains 2-hydro-1,3-perfluoroadamantandiol by 25.4% as an impurity.

2): 3-hydroxy-1-perfluoroadamantyl acrylate and 1,3-perfluoroadamantyl diacrylate contain as impurities, 2-hydro-3-hydroxy-1-perfluoroadamantyl acrylate by 10.7% and 2-hydro-1,3-perfluoroadamantyl diacrylate by 18.7%, respectively.

As a result of analysis for the resultant 3-hydroxy-1-perfluoroadamantyl acrylate by nuclear magnetic resonance spectra (NMR, CDCl$_3$), there were observed the following absorption.

$^1$H-NMR {500 MHz}: at 4.95 (br, 1H,), 6.14 (d,J=10.1 Hz, 1H), 6.24 (dd,J=10.1 Hz, 1H, J=17.2 Hz, 1H,), 6.62 (J=17.2 Hz, 1H,) $^{13}$C-NMR {126 MHz}: at 125.88 (CH$_2$=), 135.96(—CH=), 158.05 (C=O), $^{19}$F-NMR {471 MHz}: at −219.30 (s, 2F), −120.69 (s, 6F), −113.61 (s, 6F)

In addition, as the results of infrared spectroscopy (IR), absorption was observed at 1765.6 cm$^{-1}$ (C=H).

The melting point measured by DSC (differential scanning calorimetry) was 69.7 to 79.5° C.

As a result of analysis for the resultant 1,3-perfluoroadamantyl diacrylate by nuclear magnetic resonance spectra (NMR, CDCl$_3$), there were observed the following absorption.

$^1$H-NMR {500 MHz} ... at 6.12 (d,J=10.9 Hz, 2H), 6.24 (d,d, J=10.9 Hz, J=16.6 Hz, 2H), 6.62 (J=16.6 Hz, 2H) $^{13}$C-NMR {126 MHz}: at 126.09 (CH$_2$=), 135.78 (—CH=), 161.55 (C=O), $^{19}$F-NMR {471 MHz}: at −219.01 (t, J=29 Hz, 2F), −121.19 (s, 2F), −120.49(d,J=249 Hz, 2F), −119.07 (d,J=264 Hz, 2F),−117.19(d,J=249 Hz, 2F), −113.81 (d,J=29 Hz, 2F), −113.49(d,J=264 Hz, 2F)

In addition, as the results of infrared spectroscopy (IR), absorption was observed at 1781.8 cm$^{-1}$(C=H).

The melting point measured by DSC (differential scanning calorimetry) was 92.4 to 106.7° C.

INDUSTRIAL APPLICABILITY

The present invention can provide a perfluoroadamantyl acrylate compound which is highly useful in wide fields of raw materials for functional resins required of optical properties and heat resistance; resin additives such as heat resistance improvers; additives such as acidity enhancers and fat-solubility enhancers; coating materials such as paint and printing ink; lubricating oil; working oil; heating/heat transfer media; adhesives; covering materials for optical fiber; pharmaceuticals; agrochemicals; intermediates and so forth.

The invention claimed is:

1. A perfluoroadamantyl acrylate compound represented by the following general formula (1)

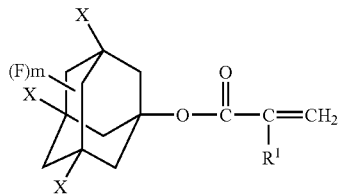

[1]

wherein R$^1$ is a hydrogen atom, a methyl group or a trifluoromethyl group; X is a fluorine atom, a hydroxy group or a CH$_2$=C(R)COO group, wherein R is a hydrogen atom, a methyl group or a trifluoromethyl group; and m is an integer of from 12 to 15.

2. A perfluoroadamantyl acrylate compound represented by the following general formula (2)

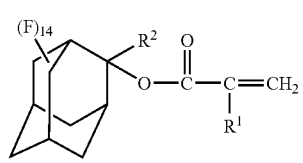

[2]

wherein R$^1$ is a hydrogen atom, a methyl group or a trifluoromethyl group; and R$^2$ is a hydrogen atom, a methyl group, an ethyl group or a perfluoroalkyl group having 1 to 4 carbon atoms:

3. A perfluoroadamantanol compound represented by the following general formula (3)

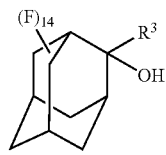

[3]

wherein R$^3$ is a methyl group, an ethyl group or a perfluoroalkyl group having 1 to 4 carbon atoms.

* * * * *